United States Patent [19]

Brasile et al.

[11] Patent Number: 5,599,659
[45] Date of Patent: Feb. 4, 1997

[54] PRESERVATION SOLUTION FOR EX VIVO, WARM PRESERVATION OF TISSUES, EXPLANTS, ORGANS AND VASCULAR ENDOTHELIAL CELLS COMPRISING RETINAL-DERIVED FIBROBLAST GROWTH FACTOR, CYCLODEXTRIN AND CHONDROITIN SULFATE

[75] Inventors: Lauren Brasile, Albany; Jolene Clarke, Ballston Spa, both of N.Y.

[73] Assignee: Breonics, Inc., Schenectady, N.Y.

[21] Appl. No.: 372,782

[22] Filed: Jan. 13, 1995

Related U.S. Application Data

[63] Continuation-in-part of Ser. No. 29,459, Mar. 11, 1993, abandoned.

[51] Int. Cl.$^6$ .............................. A01N 1/02; C12N 5/00
[52] U.S. Cl. ..................... 435/1.1; 435/1.2; 435/405; 435/406
[58] Field of Search ..................... 435/1, 2, 240.3, 435/240.31, 1.1, 1.2, 1.3

[56] References Cited

U.S. PATENT DOCUMENTS 5,455,162  10/1995  Bellamy et al. ..................... 435/71.2

OTHER PUBLICATIONS

Nakaya S et al., Proceeding Xth Int. Con. Nutrition: Sym. Pefluorochem. Art. Blood, Kyoto pp. 187–201 (1975).
Lass J H et al, Refrac & Corneal Surg. 6:92–98 (1990).
Meyer D R et al., J. Toxicol–Cut. & Ocular Toxicol 10(1&2):59–77 (1991).
Okamoto R et al., Transplant Proc 20 (1):969–71 (1988).

*Primary Examiner*—Michael G. Wityshyn
*Assistant Examiner*—S. Saucier
*Attorney, Agent, or Firm*—Hodgson, Russ, Andrews, Woods & Goodyear

[57] ABSTRACT

The present invention is directed to a new hyperosmolar preservation solution useful in supporting the simultaneous in vitro growth of, and preservation of vascular endothelial cells from large vessel and microvessel origins. In addition, the preservation solution of the present invention may be used for initial flushing, and as a perfusate for storage of organs intended for transplantation using a warm preservation technology at between 18° C. to 35° C. Among the components of the preservation solution are colloid, mucopolysaccharide, retinal-derived fibroblast growth factor and a high magnesium concentration. Also, the present invention is directed to a method for preserving, without extreme hypothermia, an organ intended to be transplanted using the preservation solution.

22 Claims, 3 Drawing Sheets

PRESERVATION SOLUTION FOR EX VIVO, WARM PRESERVATION OF TISSUES, EXPLANTS, ORGANS AND VASCULAR ENDOTHELIAL CELLS COMPRISING RETINAL-DERIVED FIBROBLAST GROWTH FACTOR, CYCLODEXTRIN AND CHONDROITIN SULFATE

This application is a continuation-in-part of U.S. patent application Ser. No. 08/029,459 filed Mar. 11, 1993, now abandoned, which is herein incorporated by reference.

BACKGROUND OF THE INVENTION

1. Field of the Invention

This invention relates generally to a solution particularly useful for supporting the in vitro growth of, and preservation of vascular endothelial cells. More particularly, the invention comprises a solution which can support ex vivo or in situ preservation without extreme hypothermia of organs, tissues, and explants.

2. Description of the Background and Related Art

A) Vascular Endothelial Cell Culture

The blood vessel wall architecture consists of three major components: the adventitia, the media, and the intima. The intima, or the lumenal area, consists of a confluent monolayer of vascular endothelial cells with tight junctions which function as a permeability barrier. It was once generally assumed that the vascular endothelial cell population was homogeneous throughout the vasculature. It is now recognized that vascular endothelial cells are a heterogeneous cell population with wide variation in morphology, function, antigen expression, and growth requirements. The history of the tissue culture of vascular endothelial cells began approximately 20 years ago when human umbilical vein endothelial cells were first cultured (Simionescu, N, Simionescu: *Histology*, Edited by L. Weiss, McGraw-Hill Book Co., 1977, pg. 373; Jaffe et al., *J. Clin. Invest.* 52:2757, 1973). Subsequent to the work with umbilical cells, endothelial cells isolated from large vessels such as aorta, saphenous vein, and vena cava, have been successfully supported in cultured by a medium such as that disclosed by Levine in U.S. Pat. Nos. 4,994,387 and 5,132,223. Vascular endothelial cells from microvessels, i.e. capillaries, arterioles, and venules, are important to studies of inflammation and neovascularization. However, microvasculature endothelial cells could be maintained in culture, but could not be passaged (Booyse et al., *Thromb. Diath. Haemorrh.* 34:825, 1975).

Since a limited number of vascular endothelial cells can be isolated from a blood vessel or a piece of tissue, typically incubation in tissue culture is required to expand the cell population or to enrich the purity of the cell preparation for laboratory procedures requiring rather large populations of vascular endothelial cells. Traditionally, the tissue culture of vascular endothelial cells relied on the use of a basal medium such as RPMI-1640 or Medium 199, supplemented with serum, heparin, and endothelial cell growth factors (Thorton et al., *Science* 22:623, 1983). The serum in this media presumably supplies the necessary nutrients, hormones, and attachment factors lacking in the basal media. A basal media which can be used without serum supplementation or minimal supplementation with serum may be desirable because of the economic benefits from reducing serum usage. The heparin, which is produced by most mammalian cells in tissue culture, potentiates the growth promoted by the endothelial cell growth factors. Endothelial cell growth factor is required to provide the positive signal to initiate vigorous cell replication. Heparin sulfate is the only mucopolysaccharide to date which has been recognized to potentiate the activity of growth factors in endothelial cells. It has been recognized since 1956 that heparin-like materials were involved in the process of cell division. However, very little biochemical evidence exists to identify the exact physiologic role of heparin sulfate. There is some discrepancy in the literature as to how effective heparin supplementation is in supporting the growth of microvessel endothelial cells. Heparin and dextran sulfate have been shown to increase bovine capillary endothelial cell migration. However, neither heparin nor dextran sulfate has any effect on capillary endothelial cell proliferation (Azizkhan et al., *J. Exp. Med.* 152:931, 1980; Zetter, *Diabetes* 30:24, 1981). In contrast, in other studies, human capillary endothelial cells have been maintained in long term culture with heparin sulfate supplementation (Jarrell et al., *J. Vas. Surg.* 1(b):758, 1984). While other mucopoly-saccharides have been previously tested for their ability to support the growth of vascular endothelial cells, to date only heparin sulfate has been recognized and used for this purpose (Folkman et al.: Cold Spring Harbor, Cell Proliferation, 1982).

Primary cultures of microvessel endothelial cells are fragile. If contaminating cell types, most notably capillary pericytes, are eliminated, the endothelial cells can be maintained undisturbed, and passage is now possible (Goetz et al., *In Vitro Cell Dev. Biol.* 21:172, 1985). By using isolation techniques which enrich the microvessel endothelial cell population and with optimizing culture conditions, it has been reported that endothelial cells can be maintained for up to 12 passages with cloned capillary endothelial cells, and for only 5 passages for microvessel cells, i.e. venules and arterioles (Booyse et al., *Thyromb. Diath. Haemorrh.* 34:825, 1975; Goetz et al., *In Vitro Cell Dev. Biol.* 21:172, 1985; Kern et al., *J. Clin. Invest.* 71:1822, 1983; Folkman et al., *Textbook of Rheumatology* (ed. Wm Kelley), Vol.1, pg.210, WB Saunders). However, this is substantially less cell growth than can be obtained with human umbilical vein endothelial cells. The cultivation of other fastidious cell types is even more difficult. If other cell types, most notably isolated cells of the kidney, explants, and whole tissues, are not transfected or immortalized, the period of time they can be viably maintained in vitro is quite short.

Therefore, there exists a need for a preservation solution as a tissue culture medium which has the ability to support the attachment and cultivation of vascular endothelial cells from a variety of anatomic sites. A desirable feature of such a solution is that the formulation can support the growth of large vessel and microvessel endothelial cells simultaneously, as well as being useful in the cultivation of a variety of other fastidious cell types, most notably the isolated cells of the kidney.

Different media formulations have been disclosed in the art which contain one or more components contained in the tissue culture medium of the present invention. However, none of the media formulations known in the art disclosed a) the combination of components of the tissue culture medium of the present invention, which b) support the simultaneous growth of large vessel endothelial cells and microvessel endothelial cells of c) human, murine, bovine, porcine, canine and rat origin from d) various anatomical sites including kidney, heart, brain, aorta, vena cava, and fat-drived.

Further, it is known to those skilled in the art that a basal medium used for the growth and support of, for example, a transformed cell will be different than the formulation for growth of fastidious cells, i.e. large vessel and microvessel endothelial cells. A comparison of the formulation of the present invention with representative formulations known in the art is summarized in Table 1.

caught and maintained the public's interest. In most cases transplantation is the therapy of choice for end-stage organ disease.

TABLE 1

| parameter | present invention | Ref. 1 | Ref. 2 | Ref. 3 | Ref. 4 | Ref. 5 |
|---|---|---|---|---|---|---|
| cell type | HUVEC; VEC; microvessel EC | rat pulmonary microvessel EC | HUVEC; VEC | porcine corneal VEC | murine mammary tumor | human lymphoblast line |
| basal medium | disclosed in Table 2 | DMEM & HF12 (1:1) | M199™ | EMEM with Earle salts | DMEM & HF12 (1:1) | RITC 56-1 or 80-7 |
| growth factor | retinal-derived acidic FGF* | pituitary extract & ECG | ECGF | EGF | none | none |
| MPS | heparin; CDS | none | none | heparin | CDS | none | none |
| Mg supplement | 1.24 g/L | 1 g/L | none | none | none | none |
| Serum protein | <1% FBS, BSA | 2–10% FBS | 20% FBS | 20% FBS | BSA/oleic acid/αCD | BSA/fatty acid & αCD |
| growth: dt | 17 hrs. | none stated | 17–21 hrs. for HUVEC | 39 hrs. | none stated | 24 hrs. |
| growth: tc | 3 days | none stated | 6 days | 9–16 days | none stated | 7 days |
| growth: matrix supplement | none (untreated) | vitrogen | gelatin | none | fibronectin | none |
| growth: cp | Factor VIII+, ACE+, diL-Ac-LDL+ | Factor VIII+, diL-Ac-LDL− | Factor VIII+, ACE+ | not stated | N/A, not VEC | N/A, not VEC |

Ref. 1: Tanswell et al. (1991, J. Dev. Physiol. 15:199–209)
Ref. 2: Levine et al. (U.S. Pat. No. 4,994,387)
Ref. 3: Lee et al. (1991, Kaoshiung J Med Sci 7:614–621)
Ref. 4: Kawamura et al. (1985, Dokkyo J. Med. Sci. 12:167–180)
Ref. 5: Yamane et al. (1981, Proc. Japan Acad. 57:385–389)
*- retinal derived acidic FGF (fibroblast growth factor) commercially available as ENDO GRO ™ (VEC TEC Inc.)
Abbreviations:
HUVEC- human umbilical cord vein endothelial cells;
VEC- large vessel vascular endothelial cells;
EC- endothelial cells;
DMEM & HF12- Dulbecco's modified Eagle's medium and Ham's F-12 medium;
EMEM- Eagle's minimal essential medium;
ECG- endothelial cell growth supplement;
ECGF- endothelial cell growth factor;
EGF- epidermal growth factor;
MPS- mucopolysaccharide;
Mg- magnesium containing compound;
BSA- bovine serum albumin;
FBS- fetal bovine serum;
αCD- alpha-cyclodextrin;
dt- population doubling time;
tc- time to confluence;
cp- conservation of phenotype;
ACE- angiotensin-converting enzyme, expressed when the cells are confluent in culture;
diL-Ac-LDL- the ability to take up acetylated- low density lipoprotein;
N/A- not applicable.

B) Organ Transplantation

Organ transplantation is a highly public therapeutic modality. Unlike any other medical innovation, transplantation has Living-related donor organ donation has steadily increased because of the severe organ shortage, living-related donation increased by 7% in 1990 alone. The size of the transplant waiting list grew by 37% between 1988 and 1990. During the same period, the number of organ donors grow by only 9%.

There are three major problem areas in organ donation/procurement:

1) limited organ donor pool—Most organs in the United States are procured from heartbeating cadavers; i.e., patients who succumb to head trauma and are therefore, brain dead and are maintained on life support systems. Heartbeating cadavers represent a small factor of trauma patients and therefore, represent a limited organ donor pool.

2) obtaining consent—When families are not confronted with the decision of terminating life-support systems, these families are much more likely to make the decision to donate, as in the case of corneas. Therefore, opening new avenues of organ donation where there would not be a decision to terminate life-support systems will not only provide a new source of organs, but in all probability would also increase the current rate.

3) preservation and associated problems—Why can't organs be harvested from non-heartbeating cadavers? The moment an organ donor's heart stops beating, the cessation of blood flow results in ischemia. The onset of ischemia initiates a phase of metabolic depression leading to cell death. We know that within 60 minutes, warm ischemia will lead to the necrosis of the proximal convoluted tubules. The historic approach to organ preservation involves hypothermia. The reduction of tissue temperature results in a lower metabolic activity. However, hypothermia preservation is not benign; it results in edema, alterations in permeability, and tubule damage. The principal difference between ischemia at warm and cold temperatures is the rate at which the cell injury and death occur. Therefore, warm ischemia damage represents the major obstacle to expanding the organ donor pool into the non-heartbeating cadaver population. Organs damaged by warm ischemia cannot tolerate further damage incurred by hypothermia. Until the damaging effects of ischemia can be alleviated, the donor pool cannot be expanded.

There are seven major parameters involved in the in vitro preservation of organs: 1) ischemia, 2) the effects of the mandatory hypothermia, oxygen consumption in hypothermically preserved organs, 4) ATP synthesis, 5) ion pumps, 6) alterations in permeability leading to edema and 7) reperfusion injury.

1) Ischemia

Ischemia, or the cessation of blood flow, will cause the phenomenon of no reflow, which is the failure of the circulation to return. Ischemia-mediated damage is most severe in the first and third segments of the proximal convoluted tubules and this damage is directly related to the length of ischemia. The initial effects of ischemia are from the lack of molecular oxygen for oxidative phosphorylation; which leads to the depletion of ATP stores within the mitochondria. Nucleotides are rapidly lost during ischemia and this loss is an important factor in the failure of tissue subjected to prolonged ischemia to regenerate ATP after the restoration of the blood supply.

2) Hypothermia

Currently, all preservation technology is dependent upon hypothermia to diminish the effects of ischemia. The benefits of hypothermia were recognized early on, when in 1937 Bickford and Winton noted that hypothermia prolonged the duration of tissue survival. Hypothermia exerts its beneficial effect by diminishing the oxygen demand of the organs and also by reducing the metabolic rate. Normal oxygen consumption by the kidney is high, approximately 6.3 ml/min. This oxygen consumption is reduced to about half at 30° C. and to less than 5% at 4° C. Most organs are stored at temperatures ranging from 4°–10° C. Similarly, below 22° C. a cessation of glomerular filtration occurs and below 18° C. tubular activity is inhibited. Most enzyme systems functioning at normothermia show an approximately two-fold decrease for every ten degrees decrease in temperature.

However, the side-effects of hypothermia are not benign. Cold-induced damage entails organ swelling, loss of endothelial cell integrity, acute tubular necrosis (ATN), inhibition of the ion pumps and intracellular acidosis. In fact, hypothermia may be the rate-limiting factor in organ preservation. To control this cold-induced damage, all clinical perfusates employ a variety of impermeants and colloids to control cell swelling.

3) Oxygen Consumption

Supplying adequate oxygen delivery to the organs was a major obstacle to success in early studies of organ preservation. Oxygen consumption in the kidney is high and this oxygen consumption correlates with renal transport processes.

Hypothermia, while reducing the rate of metabolism and oxygen consumption, also blocks the effective utilization of oxygen by tissues. At normal physiologic temperatures, the phospholipids making up the cell membranes are highly fluid. Under the hypothermic conditions utilized in organ preservation, the lipid bilayer experiences a phase-change and becomes gel-like, with greatly reduced fluidity. This essentially frozen lipid in the cell membranes negates the utilization of oxygen, even in the presence of a high oxygen-tension. Without the required oxygen, the metabolic consequence for preserved organs is glycolysis.

4) ATP

Most ATP is synthesized in mitochondria via oxidative phosphorylation. The mitochondria utilize oxygen and substrate to convert ADP to ATP and in the process reduce oxygen to $H_2O$. This controlled reduction requires the addition of four electrons. The cytochrome oxidase complex accomplishes this in one step. In doing the reduction in one step, toxic free radical intermediates are not generated.

Ischemia, whether warm or cold, initiates a rapid fall in cellular ATP levels. ATP can be readily resynthesized from adenosine once oxidative phosphorylation resumes at normothermia. Without oxidative phosphorylation, glycolysis is the only means of producing ATP. However, glycolysis is twenty times less efficient than oxidative phosphorylation. The salvage pathway of ATP production produces reactive oxygen species in the process of metabolizing hypoxanthine to xanthine and xanthine to uric acid by means of xanthine dehydrogenase. These toxic free radical intermediates include the superoxide anion radical, hydrogen peroxide and hydroxyl radical. Mitochondria normally maintain efficient control systems generating minimal levels of free radicals. Scavengers, which effectively reduce the small amount of these intermediates generated under normal conditions, abound in vivo.

The depletion of ATP causes a shutdown of the sodium pump, active $Ca^{++}$ extrusion stops, fatty acid accumulates and degraded phospholipids are not regenerated. Acidosis develops because the protons released during the synthesis of ATP cannot be converted to $H_2O$ by normal oxidative metabolism.

3) Ion Pumps

The major impact of ATP depletion is the shutdown of the ion pumps, in particular, the sodium pump. The sodium pump is responsible for maintaining the intracellular balance of sodium and potassium and for normal cell volume regulation. The pump exchanges sodium for external potassium.

The lack of ATP to drive the pumps results in increased intracellular sodium, more than there being a fall in potassium. The vascular endothelial cells can then swell to double their thickness very quickly. This swelling leads to alterations in permeability resulting in leaky endothelium. If the supply of energy is reestablished before the death of the cells occurs, the process can be reversed and cell volume returns to normal.

6) Edema

Therefore, the preservation of membrane integrity is probably the major fundamental issue to organ preservation. In all cases where metabolism is inhibited, the result is edema due to increased intracellular $H_2O$ content. The development of leaky endothelium leads to a reduction in blood flow in the medulla which leads to a secondary necrosis of the tubules, which then leads to obstruction and a reduction of glomerular filtration, urine flow and urine concentrating capacity. Therefore, the damage to the endothelium plays a major role in the subsequent renal damage secondary to the preservation.

7) Reperfusion Injury

The overall effect of hypothermic preservation is tissue hypoxia. Cold preservation followed by rewarming leads to reperfusion injury. Reperfusion injury following hypothermia is a well established concept and its main focus in on the endothelium. Toxic free radical intermediates initiate an injury cascade involving cellular derangement, leukocyte/platelet adhesion and hypercoagulation. Various scavengers and agents have been used such as superoxide dismutase (SOD) and catalase. Calcium antagonists such as chlorpromazine and prostacyclin and its analog have been used with varying degrees of success. Obviously, it is more important to avoid the generation of these radicals rather than to attempt to eliminate them.

It is apparent that the degree of preservation/reperfusion injury is the direct result of the duration of the cold preservation, and not the reperfusion, since reperfusion after short periods of cold ischemia does not lead to graft injury. The extent of free radical production is related to the length of the cold preservation. Likewise, blood cell adhesion is directly related to the preservation damage.

Hypothermia is the essential foundation of current technology used in organ preservation. All recent progress in organ preservation can be traced directly to maneuvers used to control the very damage caused by the hypothermia itself; namely using impermeants and colloids to control cell swelling, pharmacologic agents to stop nucleotide waste, and to limit reperfusion injury while maintaining the membrane integrity.

For example, the third generation of perfusates, most notably the UW solution or VIASPAN™ (Belzer et al., Transpl. 33:322–323, 1986), are totally synthetic solutions devoid of all animal protein. VIASPAN™ uses HES to avoid toxicity. There are eleven ingredients in the VIASPAN™ solution:

| | |
|---|---|
| phosphate buffer | to prevent acidosis |
| adenosine | a precursor for ATP synthesis, it also has vasodilating properties and is a platelet inhibitor |
| magnesium | cofactor for cation-dependent events |
| allopurinol | xanthine oxidase inhibitor to block oxygen radical production |
| glutathione | to assist in handling oxidative stress and for its reducing capabilities during lipid peroxidation, which may be important during reperfusion |
| HES | a colloid to prevent expansion of the extracellular space |
| raffinose | provides osmotic support |
| lactobionate | a major organic impermeant anion, since it does not permeate the membrane and therefore, prevents cell swelling |
| ions | it is also an intracellular-like solution, high in potassium. |

It is of interest to note that replacing potassium ions with sodium ions in the VIASPAN™ solution, does not affect the quality of the preservation and some reports describe improved results, particularly in liver transplantation. VIASPAN™ is superior to previous perfusates and generally represents state-of-the-art organ preservation. However, many researchers have questioned the effectiveness of some of ingredients. There is general agreement that the lactobionate is required, while only one study found HES to be required.

There are now several offshoots of the VIASPAN™ solution, including the HTK, HP16, and Cardisol solutions using haemacel or PEG to replace the HES and other sugars to replace the raffinose and impermeants to replace the lactobionate. Today we now have the situation where a new perfusate's efficacy is usually compared to VIASPAN™.

The Future

Certainly it is clear that the existing organ donor pool must somehow be expanded. If we are to expand the donor base into the nonheartbeating cadaver population, a different approach to organ preservation is needed. Warm ischemic damage represents the major obstacle to utilizing nonheartbeating cadavers and similarly, warm ischemically damaged organs cannot tolerate a second insult of hypothermic damage. Interestingly, many of the preservation related problems of severe hypothermia would be eliminated at a more moderate level of hypothermia. Future preservation ("warm preservation") may be in the range of 18°–35° C., where membrane lipids are in a more normal state. Almost everything that occurs at 37° C. also occurs at 20° C., but at a slower rate. More moderate hypothermia would help to: prevent toxic free radicals rather than using scavengers at the time of reperfusion, eliminate vasospasm, support oxygen utilization and raise the metabolic rate during preservation. Concordant with using nonheartbeating cadavers, there will be a need to develop in vitro parameters of graft viability. And there will probably be a need of organ specific perfusates, designed to support a higher level of metabolism during warm preservation techniques.

Therefore, there is a need for a preservation solution useful for initial organ flushing and as a perfusate for in situ or ex vivo preservation of organs for transplantation using a warm preservation technology which minimizes, or even repairs, damage due to warm ischemia, and which supports the organ near normal metabolic rate. A desirable feature of using such a solution is that organ preservation may be extended further by increasing metabolic activity, by eliminating severe hypothermia, and supplying adequate oxygen and metabolite delivery to support this basal metabolism.

SUMMARY OF THE INVENTION

In accordance with one aspect of the present invention, a new formulation for a preservation solution is disclosed which supports the in vitro growth of vascular endothelial cells from large vessels and microvessels simultaneously and which further supports the cultivation of a variety of other fastidious mammalian cell types, most notably isolated cells of the kidney. The preservation solution used in tissue culture comprises a buffered basal medium containing carbohydrates, metabolites, inorganic ions, serum proteins, lipids, hormones, nitrogen bases, essential amino acids, non-essential amino acids, vitamins, reducing agents and a buffering system. The unique features of the solution of the present invention include supplementation with mucopolysaccharide which potentiates the growth of microvessel endothelial cells; supplementation with cyclodextrins which potentiate the growth of large vessel and microvessel endothelial cells, and which further has the effect of contributing to a higher osmolarity; and a high magnesium ($Mg^{++}$) concentration which also potentiates the growth and preservation of vascular endothelial cells. The high osmolarity leads to alterations in the cell volume regulation which prevents swelling and facilitates the preservation of cellular integrity of cells in culture with the medium of the present invention. In accordance with this aspect of the present invention, the buffered basal medium supplemented with mucopolysaccharide, cyclodextrin and $Mg^{++}$, may be supplemented further with one or more of the following components, or their functional equivalents, to improve the in vitro preservation of cells, particularly depending on the mammalian cell type to be cultured: a fibroblast growth factor; bovine albumin (BSA); insulin; transferrin; cholesterol; pyruvate; heparin; and a serum supplement.

According to another aspect of the present invention the buffered basal medium supplemented with mucopolysaccharide, cyclodextrin and $Mg^{++}$, and having a high osmolarity, is used as a preservation solution for the initial organ flushing, and/or as a perfusate for in situ or ex vivo preservation of organs without extreme hypothermia. The mucopolysaccharides used in the preservation solution comprise primarily chondroitin sulfates and heparin sulfates. According to this aspect, the preservation solution of the present invention may be supplemented further with one or more of the following components, or their functional equivalents, to improve the in vitro preservation of explants, tissues, and whole organs particularly depending on the anatomic origin of the tissue: a fibroblast growth factor; bovine albumin (BSA); insulin; transferrin; cholesterol; pyruvate; a serum supplement, and supplying adequate oxygen and metabolite delivery.

The above-discussed features, and attendant advantages of the present invention will become apparent by reference to the following detailed description when considered in conjunction with the accompanying drawings.

DETAILED DESCRIPTION OF THE INVENTION

Definitions—

Figure 1:
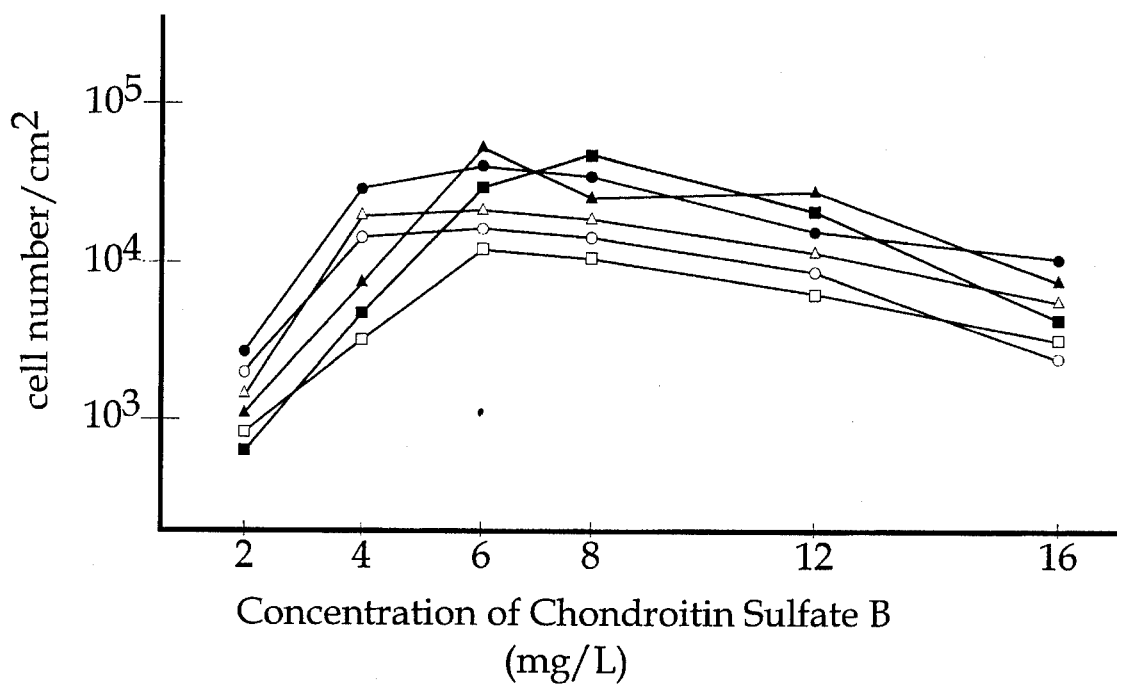
FIG. 1 is a graph representing the in-vitro cultivation and growth, during a four day period, of murine microvessel endothelial cells, isolated from various anatomic sources, in the preservation solution of the present invention supplemented with chondroitin sulfate B (4–16 mg/L) and 10% fetal bovine serum (FBS). The anatomic sources are represented as follows: ●—cardiac; ○—pancreas; ▲—liver; △—lung; ■—kidney; and □—brain.

"Hyperosmolar" is used herein to indicate that the composition has an increased osmotic concentration as compared to basal mammalian cell culture medium, and as compared to normal body fluids. Thus, "hyperosmolar" is represented by >330mOsm with an upper limit of about 600mOsm, and in a preferable range of 350–400mOsm.

"High $Mg^{++}$ concentration" is used herein to refer to an increased magnesium concentration as compared to basal mammalian cell culture medium (e.g. 98 mg/L of $MgSO_4$ in Earle's salts), and as compared to normal body fluids. Thus, for example, high magnesium concentration is represented by >1 g/L of $MgSO_4$ or the functionally equivalent concentration of other $Mg^{++}$ containing compounds and preferably in the range of 1 g/L to 4 g/L of $MgSO_4$ or functional equivalent's corresponding concentration range. "Functionally equivalent concentration of other $Mg^{++}$ containing compounds" is used herein to refer to a concentration range (expressed in g/L) of a magnesium containing compound, other than $MgSO_4$, which donates the equivalent amount in terms of available $Mg^{++}$ to cultured cells as does $MgSO_4$ in its range of 1 g/L to 4 g/L (i.e., the available $Mg^{++}$ concentration is >10mmol/L). ENDO GRO™—is a bovine retinal-derived acidic fibroblast growth factor comprising an anionic heparin binding glycoprotein effective in promoting cell proliferation with low serum concentration (VEC TEC, Inc.).

The present invention is directed to a new hyperosmolar solution particularly useful for supporting the in vitro growth of, and preservation of vascular endothelial cells, and which further supports the cultivation of a variety of other fastidious mammalian cell types, most notably isolated cells of the kidney. Also the high osmolar solution of the present invention may be used as a preservation solution for the initial organ flushing, and/or as a perfusate for storage of organs using a warm preservation technology (18°–35° C.) without extreme hypothermia. The solution has been designed to support the nutritional and metabolic needs of the vascular endothelium within a graft, thereby maintaining the integrity of the vasculature and subsequently the normal permeability of the organ. Among the components may be amino acids, ions, physiologic salts, impermeants, serum, serum proteins, sugars, lipids, attachment factors, growth factors, and mucopolysaccharides. This is the first perfusate to be able to preserve organs without concomitant extreme hypothermia; and while the studies described herein relate to the preservation of renal allografts, the application of the solution using a warm preservation technique relates to the preservation of other organs as well. While some of the components of the solution of the present invention are similar to those of other known tissue culture media, and of other known preservation (cold storage) solutions for organ transplantation with extreme hypothermia, the solution of the present invention was specifically designed to potentiate the simultaneous growth of microvessel and large vessel endothelial cells; to support the integrity of vascular endothelium within a graft; and to support more normal permeability, and metabolism without extreme hypothermia. The preservation solution of the present invention employs a cell culture-like basal medium, to which is added a variety of supplements. The enhanced ability of the solution of the present invention to serve as a medium for the culture of vascular endothelial cells, and as a preservation solution for organs for transplantation using a warm preservation technology, may be attributed to supplementation with serum albumin as a source of protein and colloid; trace elements to potentiate viability and cellular function; pyruvate and adenosine for oxidative phosphorylation support; transferrin as an attachment factor; insulin and sugars for metabolic support; and glutathione to scavenge toxic free radicals as well as a source of impermeant; cyclodextrin as a source of impermeant, scavenger, and potentiator of cell attachment and growth factors; a high $Mg^{++}$ concentration for microvessel metabolism support; mucopolysaccharides, comprising primarily chondroitin sulfates and heparin sulfates, for growth factor potentiation and hemostasis; and ENDO GRO™ as a source colloid, impermeant and growth promoter. As a result, the preservation solution of the present invention has been found to preserve organs without extreme hypothermia, and does not present the common problems encountered with cold storage perfusates—namely edema, vasospasm, depletion of ATP stores, shutdown of ion pumps, glycolysis, and the generation of cold-induced toxic free radical intermediates. The preservation solution of the present invention may provide for more efficacious preservation thereby presenting the potential to utilize an expanded donor pool—namely the nonheartbeating cadaver donors.

The solution of the present invention, useful in the in vitro cultivation and growth of vascular endothelial cells and other fastidious cell types such as isolated cells of the kidney, and useful as a preservation solution for organs for transplantation using a warm preservation technology, can be prepared according to the constituent ranges set forth in Table 2 below.

TABLE 2

COMPOSITION OF THE PRESERVATION SOLUTION OF THE PRESENT INVENTION

| | Basal Medium RANGES | Formulation 1 |
|---|---|---|
| DL-Alanine | .001–5 g/L | .12 g/L |
| L-Arginine HCl | .001–5 g/L | .14 g/L |
| DL-Aspartic Acid | .001–5 g/L | .12 g/L |
| L-Cysteine HCL●$H_2O$ | .0001–1 g/L | .00022 g/L |
| L-Cystine 2HCl | .001–5 g/L | .052 g/L |
| DL-Glutamic Acid | .001–5 g/L | .2672 g/L |
| L-Glutamine | .001–5 g/L | .2 g/L |
| Glycine | .001–5 g/L | .1 g/L |
| L-Histidine HCl●$H_2O$ | .001–5 g/L | .04376 g/L |
| L-Hydroxyproline | .001–5 g/L | .02 g/L |
| DL-Isoleucine | .001–5 g/L | .08 g/L |
| DL-Leucine | .01–5 g/L | .24 g/L |
| L-Lysine HCl | .001–5 g/L | .14 g/L |
| DL-Methionine | .001–5 g/L | .06 g/L |
| DL-Phenylalanine | .001–5 g/L | .10 g/L |
| L-Proline | .001–5 g/L | .08 g/L |
| DL-Serine | .001–5 g/L | .10 g/L |
| DL-Threonine | .001–5 g/L | .12 g/L |
| DL-Tryptophan | .001–5 g/L | .04 g/L |
| L-Tyrosine●2Na | .001–5 g/L | .11532 g/L |
| DL-Valine | .001–5 g/L | .10 g/L |
| Adenine Hemisulfate | .001–5 g/L | .02 g/L |
| Adenosine Triphosphate●2Na | .0001–1 g/L | .002 g/L |
| Adenylic Acid | .00001–1 g/L | .0004 g/L |
| Alpha Tocopherol Phosphate●2Na | .000001–1 g/L | .00002 g/L |
| Ascorbic Acid | .000001–1 g/L | .0001 g/L |
| D-Biotin | .000001–1 g/L | .00002 g/L |
| Calciferol | .00001–1 g/L | .0002 g/L |
| Cholesterol | .00001–1 g/L | .0024 g/L |
| Choline Chloride | .00001–1 g/L | .001 g/L |
| Deoxyribose | .00001–1 g/L | .001 g/L |
| Folic Acid | .000001–1 g/L | .00002 g/L |
| Glutathione (Reduced) | .000001–1 g/L | .0001 g/L |
| Guanine HCl | .00001–1 g/L | .0006 g/L |
| Hypoxanthine | .00001–1 g/L | .0006 g/L |
| Menadione (Na Bisulfite) | .000001–1 g/L | .00003 g/L |
| Myo-Inositol | .000001–1 g/L | .0001 g/L |
| Niacinamide | .000001–1 g/L | .00005 g/L |
| Nicotinic Acid | .000001–1 g/L | .00005 g/L |
| PABA | .000001–1 g/L | .0001 g/L |
| D-Pantothenic Acid Ca | .000001–1 g/L | .00002 g/L |
| Polyoxyethylenesorbitan Monooleate | .001–1 g/L | .04 g/L |
| Pyridoxal HCl | .000001–1 g/L | .00005 g/L |
| Pyridoxine HCl | .000001–1 g/L | .00005 g/L |
| Retinol Acetate | .00001–1 g/L | .00028 g/L |
| Riboflavin | .000001–1 g/L | .00002 g/L |
| Ribose | .00001–1 g/L | .001 g/L |
| Thiamine HCl | .000001–1 g/L | .00002 g/L |
| Thymine | .00001–1 g/L | .0006 g/L |
| Uracil | .00001–1 g/L | .0006 g/L |
| Xanthine●Na | .00001–1 g/L | .00069 g/L |
| Calcium chloride●$2H_2O$ | .01–2.5 g/L | .265 g/L |
| Ferric Nitrate●$9H_2O$ | .00001–1 g/L | .00144 g/L |
| Magnesium sulfate (anhydrous) | .001–5 g/L | 1.2 g/L |
| Potassium chloride | .01–5 g/L | .40 g/L |
| Sodium Acetate (anhydrous) | .001–5 g/L | .1 g/L |
| Sodium Chloride | 1–10 g/L | 6.8 g/L |
| Sodium Phosphate Monobasic (anhydrous) | .01–5 g/L | .244 g/L |
| Glucose | .1–5 g/L | 2.0 g/L |
| Insulin | .001–0.4 g/L | .01 g/L |
| Bovine serum albumin (BSA) | 5–40 g/L | 30 g/L |
| $NaHCO_3$ | .5–4.4 g/L | 4.4 g/L |
| Pyruvate | .01–2.0 g/L | .22 g/L |
| Transferrin | .001–0.8 g/L | .1 g/L |
| Serum | 1–100 ml/L | 10 ml |
| Cyclodextrin | .01–5.0 g/L | .5 g/L |

TABLE 2-continued

COMPOSITION OF THE PRESERVATION SOLUTION
OF THE PRESENT INVENTION

|  | Basal Medium RANGES | Formulation 1 |
|---|---|---|
| Mucopolysaccharide (chondroitin sulfate B) | 0.001–0.9 g/L | .004 g/L |
| ENDO GRO ™ | .002–0.04 g/L | .02 g/L |
| heparin | .01–.8 g/L | .18 g/L |

While it is contemplated that the various components of the preservation solution of the present invention may be mixed in a liter of distilled water to produce the formulation, there may exist various commercial preparations that contain many of the components, in the desired constituent ranges, of the basal medium, and that those components deficient in the particular commercial preparation may be added to that preparation to produce the formulation of the present invention. Further, some of the concentrations set forth in formulation 1 may be varied slightly without negatively affecting its function.

A first embodiment of the preservation solution of the present invention comprises a formulation comprising the components in the ranges as set forth in Table 2, wherein the solution is further supplemented by the addition of cyclodextrin, or some other impermeant, thereby contributing to a high osmolarity in the range of 330–600 mOsM and providing for optimized preservation and cultivation of a variety of mammalian cells, explants, tissues and whole organs.

A second embodiment of the preservation solution of the present invention is the formulation of the first embodiment, with a 330–600 mOsM adjusted with cyclodextrin or functionally equivalent compound (i.e., functions as an impermeant, aids in clearance of lipoprotein lipase, and helps to stabilize cell membrane factors) in the range of 0.01–5.0 g/L, and supplemented with a high concentration of $Mg^{++}$ (greater than 10 mmol/L) illustrated by the addition of $MgSO_4$ in the range of 1–4 g/L providing for superior growth and preservation of a wide range of mammalian cells, explants, tissues and whole organs.

A third embodiment of the preservation solution of the present invention is the formulation according to the second embodiment, and further supplemented with mucopolysaccharides, such as heparin sulfate and chondroitin sulfate B, in the range of 0.1–900 mg/L thereby supporting optimized preservation and growth of endothelial cells from a variety of anatomic sites, as well as a variety of other mammalian cells and tissues.

A fourth embodiment of the preservation solution of the present invention is the formulation according to the third embodiment, and further supplemented with a fibroblast growth factor such as ENDO GRO™, in the range of 20–400 μg/ml thereby supporting the optimized preservation and cultivation of endothelial cells from large vessel and microvessel cells, as well as kidney cells and a variety of other mammalian cells and tissues.

A fifth embodiment of the preservation solution of the present invention is the formulation according to the fourth embodiment, and further supplemented with bovine serum albumin in the range of 5–40 g/L thereby supporting the optimized preservation and cultivation of endothelial cells from large vessel and microvessel cells, as well as kidney cells and a variety of other mammalian cells and tissues.

A sixth embodiment of the preservation solution of the present invention is the formulation according to the fifth embodiment, and further supplemented with insulin in the range of 1–400 mg/L thereby supporting the optimized preservation and cultivation of endothelial cells from large vessel and microvessel cells, as well as kidney cells and a variety of other mammalian cells and tissues.

A seventh embodiment of the preservation solution of the present invention is the formulation according to the sixth embodiment, and further supplemented with transferrin in the range of 10–800 mg/L thereby supporting the optimized preservation and cultivation of endothelial cells from large vessel and microvessel cells, as well as kidney cells and a variety of other mammalian cells and tissues.

An eighth embodiment of the preservation solution of the present invention is the formulation according to the seventh embodiment, and further supplemented with cholesterol in the range of 0.1–100 mg/L thereby supporting the optimized preservation and cultivation of endothelial cells from large vessel and microvessel cells, as well as kidney cells and a variety of other mammalian cells and tissues.

A ninth embodiment of the preservation solution of the present invention is the formulation according to the eighth embodiment, and further supplemented with pyruvate in the range of 10–2000 mg/L thereby supporting the optimized preservation and cultivation of endothelial cells from large vessel and microvessel cells, as well as kidney cells and a variety of other mammalian cells and tissues.

A tenth embodiment of the preservation solution of the present invention is the formulation according to the ninth embodiment, and further supplemented with heparin in the range of 10–800 mg/L thereby supporting the optimized preservation and cultivation of endothelial cells from large vessel and microvessel cells, as well as kidney cells and a variety of other mammalian cells and tissues.

An eleventh embodiment of the preservation solution of the present invention is the formulation according to the tenth embodiment, and further supplemented with serum in the range of 1–100 ml/L thereby supporting the optimized preservation and cultivation of endothelial cells from large vessel and microvessel cells, as well as kidney cells and a variety of other mammalian cells and tissues.

The following examples further illustrate the use of the preservation solution of the present invention in the in vitro cultivation and growth of vascular endothelial cells, and as a perfusate for organ preservation using a warm preservation technology.

EXAMPLE 1

The ability of the preservation solution of the present invention, according to formulation 1 and as illustrated in Table 2, to support the growth of murine microvessel endothelial cells from six different anatomic sites was evaluated in tissue culture. Microvessel endothelial cells were isolated from tissue collected from heart, pancreas, liver, lung, kidney, and brain. The respective tissues were collected aseptically and stored at 4° C. in media containing antibiotics. The tissues were minced and incubated in a 0.2% collagenase solution for digestion. The digested material was passed through nylon mesh screens to remove the large tissue fragments. The filtrate was then layered onto a 45% percoll gradient and centrifuged at 10,000×g for 20 minutes. The layer of microvessel endothelial cell tufts were collected and washed. The microvessel endothelial cells were diluted by limited dilution for cloning inoculation into 96 well tissue culture plates. After incubation in culture at 37° C., the cells were evaluated for expression of Factor VIII. Monolayers of fibroblasts served as negative controls in the Factor VIII antigen expression, whereas umbilical vein endothelial cells served as the positive controls. Those cells expressing Factor VIII antigen and morphologically exhibiting properties of endothelial cells were pooled and mass cultured for each of the different anatomic sites by seeding 25 cm² flasks at a cell concentration of 5×10³/cm. After four days the microvessel endothelial cells were harvested and counted. The results, shown in FIG. 1, are reported as the mean cell density for three replicate cultures. As shown in FIG. 1, the preservation solution of the present invention provides for vigorous cell growth of microvessel endothelial cells from six different anatomic sources. The preservation solution was also used to support the growth of large vessel endothelial cells in culture, as indicated in this example by the positive control. The microvessel endothelial cells grown in the preservation solution of the present invention retained the vascular endothelial cell phenotype of expression of Factor VIII$^+$, ACE$^+$, and diL-AC-LDL$^+$.

EXAMPLE 2

With the materials and methods according to Example 1, the preservation solution of the present invention was tested for the ability to support growth of large vessel and microvessel endothelial cells isolated from different mammalian species including of porcine, bovine, rat, murine and canine origin; and microvessel endothelial cells isolated from various anatomical sites including kidney, heart, brain, aorta, vena cava, pancreas, liver and fat-drived. Large vessel endothelial cells were isolated using methods known in the art, while microvessel endothelial cells were isolated according to the methods in Example 1. The preservation solution of the present invention provided for vigorous cell growth of the large vessel and microvessel endothelial cells from the different mammalian species of origin and the different anatomic sources tested. Further, the large vessel and microvessel endothelial cells grown in the preservation solution of the present invention retained the vascular endothelial cell phenotype of expression of Factor VIII$^+$, ACE$^+$, and diL-AC-LDL$^+$. Thus, unlike prior art formulations as represented in Table 1, the preservation solution is a basal mammalian cell culture medium which has the ability to support the attachment and cultivation of vascular endothelial cells from a variety of anatomic sites, and can support the growth of large vessel and microvessel endothelial cells simultaneously, as well as being useful in the cultivation of a variety of other fastidious cell types, most notably the isolated cells of the kidney. Further, unlike the prior art formulations, the preservation solution of the present invention does not require a matrix supplement, and contains comparatively little serum supplementation, for cell attachment.

EXAMPLE 3

Figure 2:
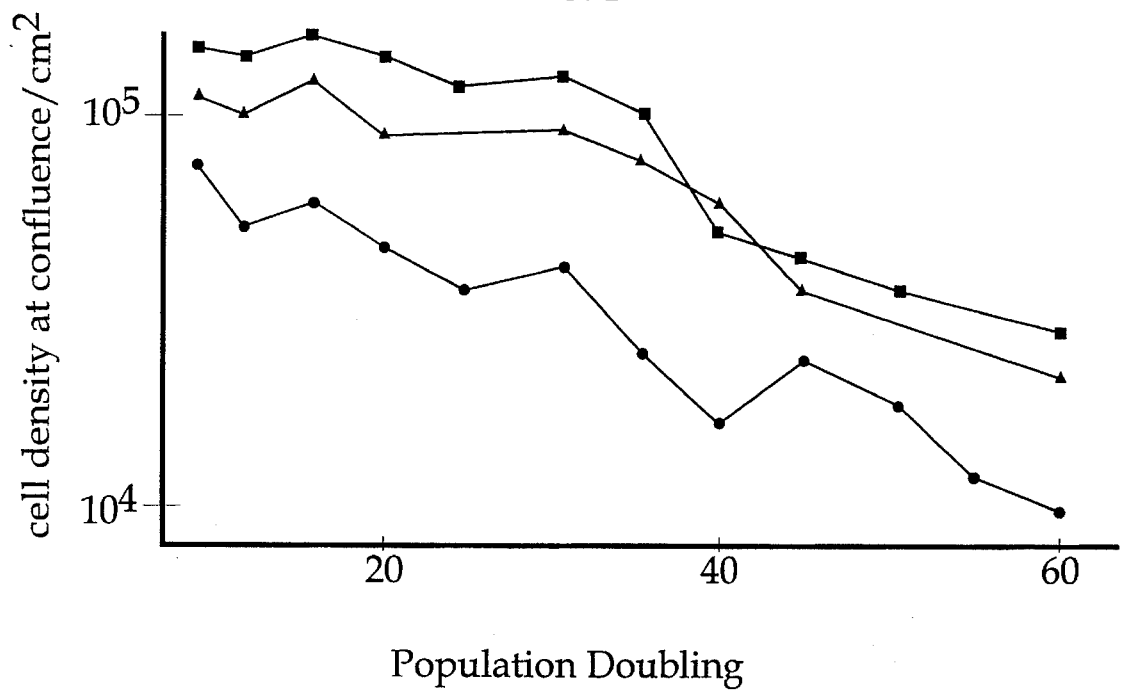
FIG. 2 is a graph representing the ability of the formulation of the preservation solution of the present invention supplemented with two concentrations of serum, compared to control medium, to support the proliferation of murine microvessel endothelial cells derived from kidney. The formulations are represented as follows: ●—control medium comprising DME:HF12 (1:1) supplemented with 10% FBS, 20 µ/ml ENDO GRO™ (VEC TEC, Inc.), 90 µg/ml heparin sulfate with antibiotics; ■—preservation solution supplemented with cyclodextrin and $Mg^{++}$, further supplemented with 10% FBS; and ▲—preservation solution supplemented with cyclodextrin and $Mg^{++}$, further supplemented with 0.5% FBS and mucopolysaccharide (5 µg/ml chondroitin sulfate B).

The ability of the preservation solution of the present invention to support the proliferation of murine microvessel endothelial cells was compared to a control media. Microvessel endothelial cells were derived from kidney and initiated into culture as described in Example 1. The microvessel endothelial cells were then seeded in triplicate at a cell concentration of 5×10³/cm² in either formulation 1 in Table 2 supplemented with 10% serum, and without mucopolysaccharide; formulation 1 supplemented with 0.5% serum and chondroitin sulfate B (5 µg/ml); or the control medium comprising DME:HF12 (1:1) supplemented with 10% FBS, 20 µg/ml ENDO GRO™, 90 µg/ml heparin sulfate and antibiotics. The individual cultures were subcultured weekly. After the first and tenth passage the microvessel endothelial cells were evaluated for the presence of a normal phenotype. The cultured cells were followed for the expression of Factor VIII antigen and angiotensin converting enzyme, using an indirect immunoperoxidase assay, and diL-Ac-LDL using a fluorescence assay (incubation in 1,1-Dioctadecyl-3,3,3.3-tetramethyl-indocarbscyamine perchlorate at 37° C.). The expression of these endothelial cell markers remained stable on microvessel cells cultured in the preservation solution of the present invention, and could be detected in all such cultures tested. The cell density at subculture versus the cumulative population doubling level for the murine microvessel endothelial cells was determined. The results, illustrated in FIG. 2, indicate that the formulation of the preservation solution of the present invention provided substantially improved, long-term prolifera- tive capabilities in supporting the growth of microvessel endothelial cells as compared to the control medium. In addition, the formulation supplemented with very little serum (<1%) yielded results functionally equivalent to the formulation supplemented with much higher concentrations of serum (10%). For example, using the preservation solution of the present invention to culture microvessel endothelial cells resulted in a time to confluence of three (3) days, and a population doubling time of just seventeen (17) hours.

EXAMPLE 4

The preservation solution of the present invention was varied in content in a step-wise fashion to evaluate the role of certain components in supporting or enhancing the growth of murine microvessel endothelial cells. The particular components varied included trace elements, antioxidants, cations, and lipids. Murine microvessel endothelial cells were isolated from heart and initiated into culture as described in Example 1. Microvessel endothelial cells were seeded at a density of 2×10³ cells/cm² in triplicate and cultured in the preservation solution of the present invention (Formulation 1, Table 2, "control" containing all supplements), or the preservation solution with 0.5% FBS and supplemented as in formulation 1 but minus a particular additive as indicated below in Table 3. On day four the cells were harvested and counted on a hemacytometer. The data listed in Table 3 represent the mean of triplicate cultures.

TABLE 3

Murine Heart Microvessel Endothelial Cells
($\times 10^5$ cells/cm²)

| Parameter | Formulation 1 (see Table 2) | |
|---|---|---|
| | minus additive | Control |
| Mg$^{++}$ | 11.4 | 18.4 |
| cyclodextrin | 15.6 | 18.2 |
| serum albumin | 11.1 | 18.1 |
| insulin/transferrin/alanine | 17.4 | 18.0 |
| pyruvate/heparin | 16.4 | 17.6 |

EXAMPLE 5

Figure 3:
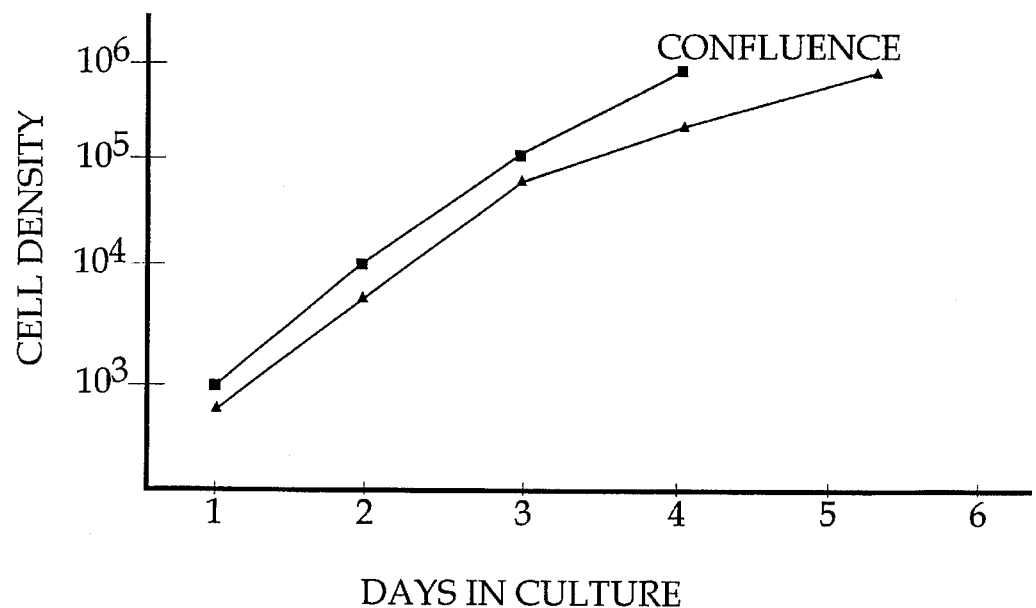
FIG. 3 is a graph representing the ability of a supplement of chondroitin sulfate to enhance large vessel endothelial cell growth in culture. ▲—is a basal medium supplemented with serum, ECGF, and heparin. ■—is a basal medium formulation containing the same concentrations of $Mg^{++}$ and heparin as in ▲, containing ENDO GRO™, and substantially differing from ▲ only by the presence of chondroitin sulfate.

The preservation solution of the present invention was varied for comparison purposes to evaluate the role of chondroitin sulfate in supporting or enhancing the growth of large vessel endothelial cells. Large vessel endothelial cells were isolated using methods known in the art and then cultured in the following medium formulations. As illustrated in FIG. 3, a basal medium similar to that described in Reference 2 of Table 1 (including Medium 199 supplemented with serum, ECGF, and heparin) (FIG. 3, ▲) was compared to a medium according to formulation 1 of Table 2 (with a $Mg^{++}$ reduced to the concentration found in Medium 199, and supplemented only with serum, ENDO GRO™, heparin, and chondroitin sulfate) (FIG. 3, ■). Thus, the two different formulations shown in FIG. 3 had the same concentrations of $Mg^{++}$ and heparin, and substantially differed only by the presence (■) or absence (▲) of chondroitin sulfate. FIG. 3 shows that chondroitin sulfate is a supplement in the basal mammalian cell culture medium which supports the attachment and cultivation of large vessel endothelial cells. Taken together with the disclosure of Example 1 and as illustrated in FIG. 1, chondroitin sulfate is a supplement which provides for vigorous growth of both large vessel and microvessel endothelial cells.

EXAMPLE 6

Figure 4:
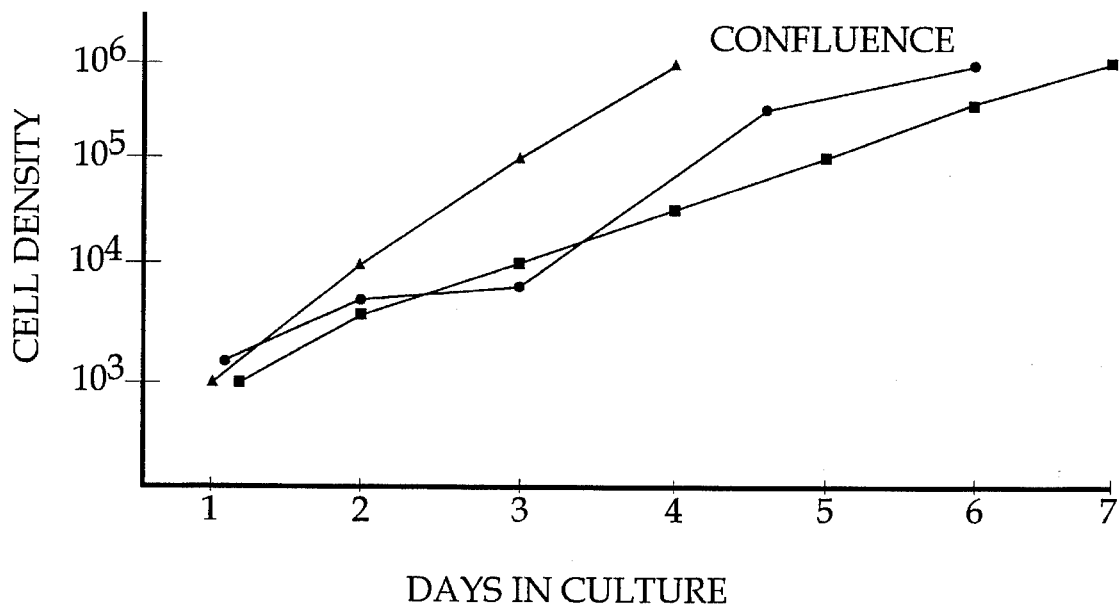
FIG. 4 is a graph representing the ability of a supplement of different growth factors to enhance large vessel endothelial cell growth in culture. ▲—is a basal medium comprising formulation 1 supplemented with ENDO GRO™ (200mg/L); ■—is a basal medium comprising formulation 1 supplemented with ECGF (200mg/L); and ■—is a basal medium comprising formulation 1 supplemented with FGF-1 (200mg/L).

The preservation solution of the present invention was varied for comparison purposes to evaluate the role of growth factors in supporting or enhancing the growth of large vessel endothelial cells. Large vessel endothelial cells were isolated using methods known in the art and then cultured in the following medium formulations. As illustrated in FIG. 4, a basal medium according to formulation 1 of Table 2 was varied only by the growth factor supplement. Thus, the three different formulations shown in FIG. 4 substantially differed only by the type of growth factor added (▲—ENDO GRO™, 200mg/L; ■—ECGF, 200mg/L; and ●—FGF-1, 200mg/L). FIG. 4 shows that the presence of ENDO GRO™, in concentration as used in formulation 1 of Table 2, is a supplement in the basal mammalian cell culture medium which enhances the growth of both large vessel and microvessel endothelial cells when compared to the medium containing equivalent amounts of two other commercially available growth factors, ECGF and FGF-1.

EXAMPLE 7

Figure 5:
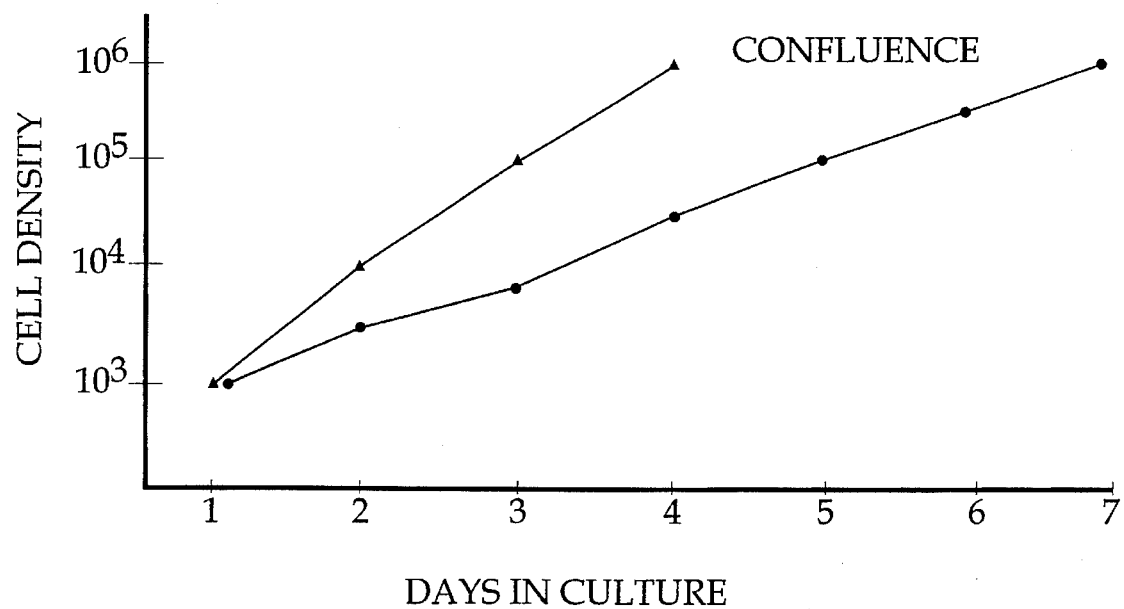
FIG. 5 is a graph representing the ability of magnesium in high concentrations to enhance microvessel endothelial cell growth in culture. ▲—is a basal medium comprising formulation 1 supplemented with $MgSO_4$ (1.30g/L); and ●—is a basal medium comprising formulation 1 supplemented with $MgSO_4$ (0.097g/L).

The preservation solution of the present invention was varied for comparison purposes to evaluate the role of magnesium in supporting or enhancing the growth of microvessel endothelial cells. Microvessel endothelial cells were derived from kidney and initiated into culture as described in Example 1. As illustrated in FIG. 5, a basal medium according to formulation 1 of Table 2 was varied only by the magnesium concentration. Thus, the two different formulations shown in FIG. 5 substantially differed only by the amount of $MgSO_4$ (anhydrous) added (▲—1.30g/L; and ●—0.097g/L, the concentration in Medium 199). FIG. 5 shows that the presence of magnesium in high concentrations (▲), as used in formulation 1 of Table 2, is a supplement in the basal mammalian cell culture medium which particularly enhances vigorous growth of microvessel endothelial cells when compared to concentrations of magnesium typically used in a basal mammalian cell culture medium.

EXAMPLE 8

The preservation solution of the present invention was evaluated for its capabilities as a perfusate in the storage of allografts using warm preservation techniques without extreme hypothermia. A total of ten canine and twelve kidneys were used to evaluate if the perfusate could be beneficial in maintaining flow characteristics and histology in the kidneys after circulatory arrest. The kidneys were flushed with the preservation solution of the present invention, using formulation 1 in Table 2, within 45 minutes postmortem. In this storage protocol, the organs remained in situ for time periods up to 12 hours and ex vivo for up to 18 hours. During the storage period, the pH may be effectively regulated by closely monitoring the pH and appropriately adjusting the flow of a gas mixture consisting of $O_2$ and $CO_2$. Histologic studies were performed to examine the integrity of the renal microvasculature. The tissue was formalin-fixed, processed in alcohol in an automatic tissue processor and then embedded in paraffin. Four micron sections were stained with hematoxylin and eosin (H&E). A second section is stained with periodic acid/Schiff reagent (PAS). The slides were examined without knowledge of treatment to assess preservation and histopathologic changes. As illustrated in Table 4, even after 45 minutes of warm ischemia, followed by 16 hours of preservation in the preservation solution of the present invention, good preservation was obtained. Edema of the organ was minimal (<5% net weight gain) in kidneys using this storage technique. The histologic findings showed no evidence of tubular or glomerular damage in kidneys stored in the preservation solution. Thus, the preservation solution of the present invention may be used as a perfusate in storage at near physiologic conditions (warm preservation without extreme hypothermia) without loss of viability of the preserved organ, and with preservation of the integrity of the renal microvasculature.

TABLE 4

| The Preservation Solution as a Perfusate N = 25 kidneys | |
|---|---|
| mean pressure | 50 mmHg |
| mean flow rate | 100 cc/minute |
| oxygen consumption | 2.41–4.7 ml/minute |
| diuresis | urine produce in all cases |
| histology | all normal |
| pH range (perfusate) | 7.32–7.46 |
| edema | <5% net weight gain |

In the studies of this example, in several cases the bladders and ureters were removed en bloc with the kidneys. The production of urine was found to be dependent upon both temperature and pressure. Temperatures above 22° C. with a concordant perfusion pressure above 30mmHg led to the formation of urine.

EXAMPLE 9

Non-perfusion storage of kidneys in the preservation solution of the present invention was compared to perfusion storage of kidneys with the preservation fluid as the perfusate. The methods used were similar to the methods outlined in Example 8 except that in each pair of kidneys, one was subjected to circulation with the perfusate at 30° C. and with a systolic pressure maintained at 60mmHg during the storage period, whereas the other kidney of the pair was stored in the perfusate at 25° C. without perfusion. After the initial flushing with approximately 500cc of the perfusate, the kidneys for perfusion storage were connected to a MOX-100 transport unit which circulated the perfusate, while maintaining vascular flow at the rate of approximately 170–200cc per minute through the period of perfusion. Circulation through the organ via a transport unit enabled the removal of toxic metabolic wastes. After an 18 hour storage period, histologic studies were performed on the perfused kidneys to examine the integrity of the renal microvasculature. Histologic findings indicated that the glomeruli and tubules were intact and normal in appearance after 18 hours of warm preservation with the perfusion storage using the preservation solution of the present invention as the perfusate. Kidneys subjected to non-perfusion storage with the perfusate were maintained at 25° C. for 24 hours and then evaluated by histologic studies. For the most part, the histologic findings in kidneys preserved by the non-perfusion storage were similar to those found in the kidneys preserved by perfusion storage. However, there was some indication of tubule drop-out, an early sign of tubule damage, which was focal and peripheral in the non-perfused kidneys. Thus, perfusion storage may be important for optimal warm preservation using the preservation solution of the present invention as a perfusate in maintaining organs without loss of viability of the preserved organ, while preserving the integrity of the renal microvasculature. The preservation period illustrated in these results, using the preservation solution of the present invention as a perfusate in a warm preservation technique, are comparable to the preservation periods of similar studies using VIASPAN™ as a perfusate in organ preservation with extreme hypothermia (at 4° C.).

It should be understood that the embodiments and the examples of the present invention, as described herein, are for purposes of illustration only, and not limitation, and any changes or modifications as will become apparent to one of ordinary skill in the art from the foregoing description and accompanying figures are intended to be included within the scope of the appended claims and the equivalents thereof.

We claim:

1. A solution with an osmolarity of 330 to 600 mOsm comprising:

(a) a cell culture medium;

(b) Mg++ in a concentration greater than 10mmol/L; and (c) chondroitin sulfate, heparin, cyclodextrin, insulin, cholesterol, pyruvate, and retinal-derived fibroblast growth factor in concentrations sufficient to preserve tissues, explants, vascular endothelial cells, and organs at temperatures ranging from about 18° C. to about 35° C.

2. The solution according to claim 1, further comprising transferrin.

3. The solution according to claim 2, containing from about 0.01 to about 0.4g/L of transferrin.

4. The solution according to claim 1, containing from about 0.1 to about 1g/L of cyclodextrin.

5. The solution according to claim 1, containing from about 1 to about 50 mg/L of chondroitin sulfate.

6. The solution according to claim 1, wherein the Mg++ is added in the form of magnesium sulfate.

7. The solution according to claim 6, containing from about 1.0 to about 4.0 g/L of magnesium sulfate.

8. The solution according to claim 1, containing from about 0.02 to about 0.4g/L of said retinal-derived fibroblast growth factor.

9. The solution according to claim 1, further comprising serum protein.

10. The solution according to claim 9, wherein the serum protein comprises from about 1 to about 100ml/L of a serum supplement.

11. The solution according to claim 1, containing from about 0.001 to about 0.1g/L of insulin.

12. The solution according to claim 1, containing from about 0.001 to about 0.1g/L of cholesterol.

13. The solution according to claim 1, containing from about 0.1 to about 1g/L of pyruvate.

14. The solution according to claim 1, containing from about 0.01 to about 0.8g/L of heparin.

15. A method for the warm preservation of a tissue, explant, or organ intended for transplantation comprising using the solution according to claim 15 at temperatures ranging from about 18° C. to about 35° C. in a method selected from the group consisting of flushing the tissue, explant, or organ, storing the tissue, explant, or organ, perfusing the tissue, explant, or organ, and suffusing the tissue or explant.

16. The method for the warm preservation of a tissue, explant, or organ according to claim 15, comprising storing the tissue, explant, or organ in the solution.

17. The method according to claim 15, wherein the method comprises perfusing the organ in the solution.

18. The method according to claim 15, wherein the method comprises suffusing the tissue or explant in the solution.

19. A method for the warm preservation of a tissue, explant, or organ intended for transplantation comprising using the solution according to claim 2 at temperatures ranging from about 18° C. to about 35° C. in a method selected from the group consisting of flushing the tissue, explant, or organ, storing the tissue, explant, or organ, perfusing the tissue, explant, or organ, and suffusing the tissue or explant.

20. The method for the warm preservation of a tissue, explant, or organ according to claim 19, comprising storing the tissue, explant, or organ in the solution.

21. The method according to claim 19, wherein the method comprises perfusing the organ in the solution.

22. The method according to claim 19, wherein the method comprises suffusing the tissue or explant in the solution.

* * * * *

UNITED STATES PATENT AND TRADEMARK OFFICE
CERTIFICATE OF CORRECTION

PATENT NO.   : 5,599,659
DATED        : February 4, 1997
INVENTOR(S)  : Lauren Brasile It is certified that error appears in the above-identified patent and that said Letters Patent are hereby corrected as shown below:

Title page, item [54] and Column 1, lines 1-7:

"PRESERVATION SOLUTION FOR EX VIVO, WARM
PRESERVATION OF TISSUES, EXPLANTS, ORGANS AND
VASCULAR ENDOTHELIAL CELLS COMPRISING RETINAL-
DERIVED FIBROBLAST GROWTH FACTOR, CYCLODEXTRIN
AND CHONDROITIN SULFATE
should be --PRESERVATION SOLUTION FOR EX VIVO,
WARM PRESERVATION OF TISSUES, EXPLANTS, ORGANS
AND VASCULAR ENDOTHELIAL CELLS--.

Col. 20, line 21 - "solution according to claim 15" should be --solution according to claim 1--.

Signed and Sealed this

Fifteenth Day of April, 1997

Attest:

BRUCE LEHMAN

Attesting Officer

Commissioner of Patents and Trademarks